(12) United States Patent
Ujita et al.

(10) Patent No.: US 8,173,832 B2
(45) Date of Patent: May 8, 2012

(54) PROCESS FOR PRODUCING 2-ISOPROPENYL-5-METHYL-4-HEXENE-1-YL-3-METHYL-2-BUTENOATE

(75) Inventors: Katsuji Ujita, Tainai (JP); Keisuke Saeki, Tokyo (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 80 days.

(21) Appl. No.: 12/519,417

(22) PCT Filed: Mar. 28, 2007

(86) PCT No.: PCT/JP2007/056587
§ 371 (c)(1),
(2), (4) Date: Jul. 15, 2009

(87) PCT Pub. No.: WO2008/075468
PCT Pub. Date: Jun. 26, 2008

(65) Prior Publication Data
US 2010/0063314 A1   Mar. 11, 2010

(30) Foreign Application Priority Data
Dec. 19, 2006   (JP) .................. 2006-341025

(51) Int. Cl.
*C07C 67/48* (2006.01)
*C07C 69/52* (2006.01)
(52) U.S. Cl. ................ 560/218; 560/225
(58) Field of Classification Search .......... None
See application file for complete search history.

(56) References Cited

U.S. PATENT DOCUMENTS

| 3,781,333 A | 12/1973 | Kappeler et al. |
| 2009/0023941 A1 | 1/2009 | Ujita et al. |

FOREIGN PATENT DOCUMENTS

| GB | 1 244 187 A1 | 8/1971 |
| JP | 02-129144 A | 5/1990 |
| JP | 2002-187868 A | 7/2002 |
| JP | 2002-308815 A | 10/2002 |
| JP | 2003-064027 A | 3/2003 |
| WO | WO 2006/109570 A1 | 10/2006 |

OTHER PUBLICATIONS

Carey et al, Advanced Organic Chemistry, 4th Edition, 2001, Kluwer Academic/Plenum Publishers, New York, pp. 166-167.*
Hinkens et al., *Tetrahedron Letters*, 42(9): 1619-1621 (2001).

* cited by examiner

*Primary Examiner* — Paul A Zucker
(74) *Attorney, Agent, or Firm* — Leydig, Voit & Mayer, Ltd.

(57) ABSTRACT

Provided is a method capable of solving the problems associated with production of LVSA, which is a pheromone produced by female pest mealybugs, and is useful as an agrochemical pest, at an industrial large scale, and producing LVSA in a high yield. Specifically, the present invention provides a production method of 2-isopropenyl-5-methyl-4-hexen-1-yl 3-methyl-2-butenoate, comprising reacting senecioic acid with a halogenating agent to give senecioic acid halide, reacting the obtained senecioic acid halide with 2-isopropenyl-5-methyl-4-hexen-1-ol in the presence of an organic base compound and heat treating the obtained crude 2-isopropenyl-5-methyl-4-hexen-1-yl 3-methyl-2-butenoate in the presence of a basic substance at 50-250° C.

1 Claim, No Drawings

PROCESS FOR PRODUCING 2-ISOPROPENYL-5-METHYL-4-HEXENE-1-YL-3-METHYL-2-BUTENOATE

TECHNICAL FIELD

The present invention relates to a production method of 2-isopropenyl-5-methyl-4-hexen-1-yl 3-methyl-2-butenoate (hereinafter to be referred to as LVSA). LVSA is a pheromone produced by female pest mealybugs, and is useful as an agrochemical (see non-patent document 1).

BACKGROUND ART

As a conventional production method of LVSA, a method including reacting senecioic acid with thionyl chloride to give senecioyl chloride, and reacting the obtained senecioyl chloride with 2-isopropenyl-5-methyl-4-hexen-1-ol in the presence of an organic base compound is known (see non-patent document 1).
non-patent document 1: "Tetrahedron Letters", 2001, vol. 42, 9th printing, p. 1619-1621 (Scheme 1. and page 2, upper right column, lines 15-18)

DISCLOSURE OF THE INVENTION

Problems to be Solved by the Invention

The method described in non-patent document 1 is capable of producing the object LVSA without any particular problem when the amount to be produced is as small as that of a laboratory level. However, it has been clarified that an unexpected problem of low yield of LVSA occurs by an industrial large-scale production (e.g., production of not less than 1 kg per day) due to a byproduct, and the like.

It is therefore an object of the present invention to provide a production method of LVSA, which can achieve a high yield even in the case of an industrial large-scale production.

Means of Solving the Problems

According to the present invention, the above-mentioned object can be achieved by providing a production method of LVSA, which includes reacting senecioic acid with a halogenating agent to give senecioic acid halide, reacting the obtained senecioic acid halide with 2-isopropenyl-5-methyl-4-hexen-1-ol in the presence of an organic base compound to give crude 2-isopropenyl-5-methyl-4-hexen-1-yl 3-methyl-2-butenoate (hereinafter to be referred to as crude LVSA), and heat treating the crude LVSA in the presence of a basic substance at 50-250° C.

Effect of the Invention

According to the present invention, LVSA can be produced in a high yield by a simple operation even in an industrial large-scale production.

BEST MODE FOR CARRYING OUT THE INVENTION

As mentioned above, the present invention comprises
(1) a step of reacting senecioic acid with a halogenating agent to give a senecioic acid halide (hereinafter to be referred to as step 1),
(2) a step of reacting the obtained senecioic acid halide with 2-isopropenyl-5-methyl-4-hexen-1-ol in the presence of an organic base compound, subjecting the obtained reaction mixture to the below-mentioned neutralization treatment and the like as appropriate, and evaporating the solvent as necessary to give crude LVSA (hereinafter to be referred to as step 2), and
(3) a step of heat treating the crude LVSA obtained in the aforementioned (2) in the presence of a basic substance at 50-250° C. (hereinafter to be referred to as step 3).

Step 1 is explained below.

The halogenating agent is not subject to any particular limitation and a known halogenating agent can be used. Examples of the halogenating agent include thionyl chloride, thionyl bromide, sulfuryl chloride, phosphorus trichloride, phosphorus tribromide, phosphorus pentachloride, oxalyl chloride, benzyl chloride, phosgene, triphosgene, cyanuric chloride, cyanuric bromide, dichlorotriphenylphosphorane, dibromotriphenylphosphorane and the like. While any of these halogenating agents may be used, a method using thionyl chloride is described below as a representative example.

While the amount of thionyl chloride to be used is not particularly limited, it is generally preferably 0.8-1.5 mol, more preferably 1-1.2 mol, per 1 mol of senecioic acid.

While step 1 can be performed in the absence of a catalyst, it is preferably performed in the presence of a catalyst. Examples of the catalyst include N,N-dimethylformamide (DMF), hexamethylphosphoric triamide, pyridine and the like. Among these, N,N-dimethylformamide is preferably used. The catalyst may be a single agent or a combination of two or more agents. When a catalyst is used, the amount thereof to be used is not particularly limited. However, it is generally preferably 0.001-0.5 mol, more preferably 0.01-0.1 mol, per 1 mol of senecioic acid.

Step 1 is preferably performed in the presence of a solvent. Examples of the solvent include aromatic hydrocarbons such as toluene, xylene, mesitylene and the like, ethers such as tetrahydrofuran, diisopropyl ether, dibutyl ether and the like, and the like. The solvent may be a single agent or a combination of two or more agents. When a solvent is used, the amount thereof to be used is not particularly limited. However, it is generally preferably 0.4- to 5-fold by mass, more preferably 0.7- to 2-fold by mass, relative to senecioic acid.

Step 1 wherein thionyl chloride is used as a halogenating agent is performed by heating a mixture of senecioic acid, a catalyst and a solvent to be used as appropriate to 50-70° C., preferably 55-65° C., and adding thionyl chloride dropwise thereto. During the dropwise addition, the solution is preferably maintained at 50-70° C. The time of dropwise addition varies depending on the amounts of senecioic acid, thionyl chloride and the solvent to be used, and is not particularly limited. Therefore, the time can be appropriately set to maintain the temperature of the reaction mixture within a predetermined range. For example, when 5 kg of senecioic acid is used, thionyl chloride is preferably added dropwise over 10-20 hr. In addition, after completion of the dropwise addition, the mixture is preferably stirred at 50-70° C. for 10-20 hr to complete the reaction.

As the reaction proceeds after the dropwise addition of thionyl chloride is started, hydrochloric acid gas and sulfur dioxide gas are generated. To suppress production of byproduct, they are extremely preferably discharged from the reaction system during the reaction.

After the completion of step 1, the solvent is evaporated from the obtained reaction mixture under reduced pressure. Then, to sufficiently decrease the low boiling point components (hydrochloric acid gas, sulfur dioxide gas, thionyl chloride, etc.) still remaining in the residual product, it is preferable to repeat 2 to 4 times an operation to add preferably the same solvent as used for the reaction to the residual product, and distill away the solvent under reduced pressure together with the low boiling point components. While the pressure and temperature of distillation under reduced pressure are not particularly limited, the low boiling point components in the residual product can be reduced when the operation is performed, for example, at 3.3 kPa and 30-50° C. Furthermore, distillation at, for example, 3.3 kPa and 50-60° C. thereafter produces senecioyl chloride.

Step 2 is explained in the following.

The amount of 2-isopropenyl-5-methyl-4-hexen-1-ol to be used is generally preferably within the range of 0.4-1.5 mol, more preferably 0.6-1.2 mol, per 1 mol of senecioic acid halide.

Examples of the organic base compound to be used in step 2 include nitrogen-containing heterocyclic aromatic compounds such as pyridine, pyrimidine, quinoline, dimethylaminopyridine and the like: amines such as triethylamine, tributylamine, etc., and the like. Among these, pyridine is preferably used from the aspect of selectivity. The organic base compound may be used alone or a combination of two or more thereof may be used. The amount of such organic base compound to be used is generally preferably within the range of 0.6-2.5 mol, more preferably 1-2 mol, per 1 mol of senecioic acid halide.

Step 2 may be performed in the presence of a solvent. Examples of the solvent include aromatic hydrocarbons such as toluene, xylene, mesitylene and the like: ethers such as diisopropyl ether, dibutyl ether, etc., and the like. The solvent may be a single agent or a combination of two or more agents. When a solvent is used, the amount thereof to be used is not particularly limited. However, it is generally preferably within the range of 1- to 10-fold mass, more preferably 2- to 6-fold mass, relative to senecioic acid halide.

In step 2, a mixture of 2-isopropenyl-5-methyl-4-hexen-1-ol, an organic base compound and a solvent to be appropriately used is cooled to 0-10° C., and reacted by adding dropwise the senecioic acid halide obtained in step 1. During this operation, the temperature of the solution is preferably maintained at 0 to 15° C. The time of dropwise addition of the senecioic acid halide varies depending on the amounts of senecioic acid halide, 2-isopropenyl-5-methyl-4-hexen-1-ol and the solvent to be used and is not particularly limited. Therefore, the time can be appropriately set to maintain the temperature of the reaction mixture within a predetermined range. For example, when 5 kg of senecioyl chloride is used, senecioyl chloride is preferably added dropwise over 3-6 hr. In addition, after completion of the dropwise addition, the mixture is preferably stirred at 0-15° C. for 10-25 hr to complete the reaction.

After the completion of step 2, moreover, the obtained reaction mixture is preferably subjected to a neutralization and washing treatment. For example, the reaction mixture obtained in step 2 (1 L) is washed with water (1 L), 1 mol % aqueous hydrochloric acid solution (1 L), water (1 L), 5 mass % aqueous sodium carbonate solution (1 L) and water (1 L) in this order. After such neutralization and washing treatment, the solvent is evaporated under reduced pressure from the obtained organic layer as necessary to give crude LVSA.

Step 3 is explained in the following.

In step 3, the crude LVSA obtained in step 2 is treated by heating at 50-250° C., preferably 60-230° C., in the presence of a basic substance. When the temperature of the heat treatment is lower than 50° C., the yield improving effect of step 3 becomes poor, and the object of the present invention cannot be sufficiently achieved. On the other hand, when the temperature exceeds 250° C., LVSA tends to be decomposed and the yield unpreferably decreases.

Examples of the basic substance to be used in step 3 include hydrogen carbonates of alkali metal such as sodium hydrogen carbonate, potassium hydrogen carbonate and the like: carbonates of alkaline earth metal such as lithium carbonate, sodium carbonate, potassium carbonate and the like: alkali metal salts of carboxylic acid such as lithium acetate, sodium acetate, potassium acetate, sodium propionate, potassium propionate and the like: alkylamines such as triethylamine, tributylamine and the like: nitrogen-containing heterocyclic aromatic compounds such as pyridine, picoline and the like: nitrogen-containing heterobicyclic compounds such as 1,8-diazabicyclo[5.4.0]-7-undecene (DBU), 1,5-diazabicyclo[4.3.0]-5-nonene (DBN), etc. and the like. These may be used alone or two or more thereof may be used in combination. The amount of the basic substance to be used is preferably within the range of 0.1-20 parts by mass, more preferably 1-10 parts by mass, per 1 part by mass of the crude LVSA. While the time of the heat treatment varies depending on the amount of the crude LVSA, the kind and amount of the basic substance, heating temperature and the like, it is generally preferably within the range of 1-24 hr.

After the completion of step 3, LVSA can be separated and purified by successive distillation under reduced pressure (105-109° C./79-81 Pa).

Even when LVSA is produced industrially in a large-scale (e.g., production of not less than 1 kg per day), the yield of LVSA can be surprisingly improved by going through step 3. Without step 3, an industrial large-scale production of LVSA results in a drastically decreased yield of LVSA, which is due to problems of piping obstruction during purification by distillation and the like (see Comparative Examples 1-4 in the present specification). While the exact cause of such problems is not clear, it is considered that the longer reaction time necessary for scaling up permits easy generation of byproducts, and the resulting byproducts adversely affect the distillation after step 3.

2-Isopropenyl-5-methyl-4-hexen-1-ol to be used in step 2 can be produced by, for example, reacting senecioic aldehyde dimethylacetal with 3-methyl-1-buten-3-ol in the presence of an acid catalyst and reducing the obtained 2-isopropenyl-5-methyl-4-hexenal with sodium borohydride (see patent document 1).

patent document 1: JP-A-14-308815

EXAMPLES

The present invention is explained in more detail in the following by referring to Examples, which are not to be construed as limitative.

Example 1

Step 1: Production of Senecioyl Chloride

Senecioic acid (5 kg, 42.17 mol), DMF (115.9 ml, 1.49 mol) and toluene (7.5 L) were placed in a four-neck flask (inner volume 20 L) equipped with a thermometer and a stirrer, the obtained mixture was heated to 55° C., and thionyl chloride (6.55 kg, 55.07 mol) was added dropwise over 14 hr. During the dropwise addition, the temperature of the mixture was maintained at 55 to 65° C. After completion of the dropwise addition, the reaction mixture was further stirred for 8 hr while maintaining the temperature of the mixture at 55 to 65° C.

After completion of the reaction, toluene was evaporated under reduced pressure (30-35° C./3.3 kPa), and toluene (2000 ml) was added and evaporated (35-40° C./3.3 kPa).

Toluene (2000 ml) was further added and evaporated again (50-60° C./3.3 kPa), whereby the impurity was removed as much as possible. As a result, a solution (17.87 kg) of senecioyl chloride in toluene [equivalent to senecioyl chloride (4.28 kg, 36.1 mol), yield 85.6%] was obtained.

Example 2

Step 2: Production of Crude LVSA

2-Isopropenyl-5-methyl-4-hexen-1-ol (4435 g, 28.75 mol), pyridine (4026 g, 50.89 mol) and toluene (10 L) were placed in a four-neck flask (inner volume 50 L) equipped with a thermometer and a stirrer, and the obtained mixture was cooled to 5° C. Then, a solution (16.79 kg) of senecioyl chloride in toluene [equivalent to senecioyl chloride (4.02 kg, 33.92 mol)] obtained in Example 1 was added dropwise over 4.5 hr. During the dropwise addition, the temperature of the mixture was maintained at 0 to 5° C. After completion of the dropwise addition, the mixture was further stirred at 0 to 10° C. for 17 hr.

After completion of the reaction, distilled water (20 L) was added at the same temperature, and the mixture was stirred for 1 hr. After partitioning, the organic layer was successively neutralized and washed with 1 mol % aqueous hydrochloric acid solution (10 L), distilled water (10 L), 5 mass % aqueous sodium carbonate solution (10 L) and distilled water (10 L). The organic layer after neutralization and washing was concentrated to give crude LVSA (7.12 kg) [equivalent to LVSA (5.47 kg, 23.14 mol), purity 78%, yield 80.5%].

Example 3

Step 3

The crude LVSA (949 g) [equivalent to LVSA (808 g, 3.41 mol)] obtained in Example 2 and sodium carbonate (46 g, 0.434 mol) were placed in a three-neck flask (inner volume 2 L) equipped with a condenser, a thermometer and a stirrer, and the mixture was heat treated by stirring at 200° C. for 12 hr. The mixture after the heat treatment was cooled to room temperature, and the solid products (sodium hydrogen carbonate, sodium carbonate, sodium chloride, etc.) were filtered off. The filtrate was distilled under reduced pressure (105-109° C./80 Pa) using a distillation column (filler: Heli Pack) with a theoretical plate number of 23 to give LVSA (725 g, 3.06 mol, recovery rate 89.7%, purity 99.2%) having the following property.

$^1$H-NMR (300 MHz, CDCl$_3$, TMS) δ: 5.66 (1H, s), 5.07 (1H, t), 4.82 (1H, t), 4.75 (1H, s), 4.07 (2H, d), 2.42 (1H, m), 2.15 (3H, s), 2.03-2.24 (2H, m), 1.88 (3H, s), 1.70 (3H, s), 1.68 (3H, s), 1.60 (3H, s)

Example 4

In the same manner as in Example 3 except that the temperature of heat treatment was set to 250° C., an experiment was performed. As a result, LVSA (707 g, 2.98 mol, recovery rate 87.5%, purity 99.0%) was obtained.

Example 5

In the same manner as in Example 3 except that 1,8-diazabicyclo[5.4.0]-7-undecene (DBU) (66 g, 0.434 mol) was used instead of sodium carbonate (46 g, 0.434 mol), and the temperature of heat treatment was set to 62° C., an experiment was performed. As a result, LVSA (700 g, 2.95 mol, recovery rate 86.6%, purity 99.1%) was obtained.

Comparative Example 1

Distillation of Crude LVSA without Step 3

The crude LVSA (949 g) [equivalent to LVSA (808 g, 3.41 mol)] obtained in Example 2 was placed in a three-neck flask (inner volume 2 L) equipped with a condenser, a thermometer and a stirrer, and distilled under reduced pressure (105-109° C./80 Pa) using a distillation column (filler: Heli Pack) with a theoretical plate number of 10. However, the top of the distillation column and the like were clogged soon, and the object product LVSA could not be distilled off. Snecioic acid was detected in the clogged part of the distillation column.

Comparative Example 2

Distillation of Crude LVSA using Distillation Column with Low Theoretical Plate Number and without Step 3

The crude LVSA (1285 g) [equivalent to LVSA (1000 g, 4.21 mol)] obtained in Example 2 was placed in a three-neck flask (inner volume 2 L) equipped with a condenser, a thermometer and a stirrer, and distilled under reduced pressure (120° C./267 Pa) using a distillation column (filler: Heli Pack) with a theoretical plate number of 5. However, the top of the distillation column was clogged after a while, and the object product LVSA could not be distilled off. Senecioic acid was detected in the clogged part of the distillation column.

Comparative Example 3

In Step 3, when the Temperature in Heat Treatment was Changed to 20° C.

In the same manner as in Example 3 except that the temperature of heat treatment was set to 20° C., an experiment was performed. As a result, LVSA (333 g, recovery rate 41.2%, purity 72.3%) was only obtained.

Comparative Example 4

In Step 3, when the Temperature in Heat Treatment was Changed to 270° C.

In the same manner as in Example 3 except that the temperature of heat treatment was set to 270° C., an experiment was performed. As a result, LVSA was decomposed and 480 g (recovery rate 60.1%, purity 95.3%) thereof was only obtained.

Reference Example 1

Performing Step 1 and Step 2 at Small Scale, Followed by Distillation of Crude LVSA without Step 3

Step 1: Production of Senecioyl Chloride

Senecioic acid (500 g, 5 mol), DMF (11.1 ml, 0.15 mol) and toluene (650 mL) were placed in a four-neck flask (inner volume 2 L) equipped with a thermometer and a stirrer, the obtained mixture was heated to 55° C., and thionyl chloride (652 g, 5.5 mol) was added dropwise over 2.5 hr. During the dropwise addition, the temperature of the mixture was maintained at 54 to 68° C. After completion of the dropwise addition, the mixture was further stirred at the same temperature for 1 hr.

After completion of the reaction, toluene was evaporated under reduced pressure (30-35° C./3.3 kPa), and toluene (430 ml) was added and evaporated (35-40° C./3.3 kPa). Toluene (430 ml) was further added and evaporated again (50-60° C./3.3 kPa), whereby the impurity was removed as much as possible. As a result, a solution (784.9 g) of senecioyl chloride in toluene [equivalent to senecioyl chloride (418 g, 3.53 mol), yield 70.6%] was obtained.

Step 2: Production of Crude LVSA

2-Isopropenyl-5-methyl-4-hexen-1-ol (425.4 g, 2.75 mol), pyridine (325.9 g, 4.12 mol) and toluene (1.97 L) were placed in a four-neck flask (inner volume 5 L) equipped with a thermometer and a stirrer, the obtained mixture was cooled to 5° C., and the solution (727.8 g) of senecioyl chloride in toluene [equivalent to senecioyl chloride (387.9 g, 3.27 mol)] obtained in the above-mentioned step 1 was added dropwise over 1 hr (during the dropwise addition, the temperature of the mixture was maintained at 10 to 13° C.). After completion of the dropwise addition, the mixture was further stirred at 3 to 5° C. for 4.5 hr.

After completion of the reaction, distilled water (1.7 L) was added at the same temperature, and the mixture was stirred for 10 min. After partitioning, the organic layer was successively neutralized and washed with 1 mol % aqueous hydrochloric acid solution (860 mL), distilled water (830 mL), 5 mass % aqueous sodium carbonate solution (880 mL) and distilled water (830 mL). The organic layer after neutralization and washing was concentrated to give crude LVSA (689.7 g) [equivalent to LVSA (614.2 g, 2.6 mol), purity 89%, yield 94.9%].

(Distillation without Step 3)

Successively, the crude LVSA (689.7 g) [equivalent to LVSA (614.2 g, 2.6 mol)] obtained in the above-mentioned step 2 was placed in a three-neck flask (inner volume 1 L) equipped with a condenser, a thermometer and a stirrer, and distilled under reduced pressure (105° C./80 Pa) using a distillation column (filler: Heli Pack) with a theoretical plate number of 10. As a result, LVSA (546.0 g, 2.31 mol, purity 99.0%, yield 88.9%) was obtained without any particular problem.

From Examples 1-5, Comparative Examples 1-4 and Reference Example 1, it has been clarified that an industrial scale production of crude LVSA including a distillation operation without step 3 fails to achieve distillation because the top of distillation column and the like are clogged; however, "step 3" including a heat treatment in the presence of a basic substance at 50-250° C. solves the aforementioned problem in the distillation operation after step 3 and LVSA can be produced in a high purity and a high yield.

INDUSTRIAL APPLICABILITY

The present invention relates to a production method of 2-isopropenyl-5-methyl-4-hexen-1-yl 3-methyl-2-butenoate (hereinafter to be referred to as LVSA). LVSA is a pheromone produced by female pest mealybugs, and is useful as an agrochemical.

The invention claimed is:

1. A production method of 2-isopropenyl-5-methyl-4-hexen-1-yl 3-methyl-2-butenoate, comprising reacting senecioic acid with a halogenating agent to give senecioic acid halide, reacting the obtained senecioic acid halide with 2-isopropenyl-5-methyl-4-hexen-1-ol in the presence of at least one organic base compound selected from the group consisting of pyridine, pyrimidine, quinoline, dimethylaminopyridine, triethylamine, and tributylamine and heat treating the obtained crude 2-isopropenyl-5-methyl-4-hexen-1-yl 3-methyl-2-butenoate in the presence of a basic substance at 50-250° C.

* * * * *